(12) United States Patent
Lavi

(10) Patent No.: US 8,147,491 B2
(45) Date of Patent: Apr. 3, 2012

(54) MULTI-ANGLE CLAMP

(75) Inventor: Abraham Lavi, Bradenton, FL (US)

(73) Assignee: Vilex in Tennessee, Inc., McMinnville, TN (US)

( * ) Notice: Subject to any disclaimer, the term of this patent is extended or adjusted under 35 U.S.C. 154(b) by 813 days.

(21) Appl. No.: 12/215,193

(22) Filed: Jun. 25, 2008

(65) Prior Publication Data
US 2009/0018541 A1    Jan. 15, 2009

Related U.S. Application Data

(60) Provisional application No. 60/937,391, filed on Jun. 27, 2007.

(51) Int. Cl.
*A61B 17/70* (2006.01)
(52) U.S. Cl. ............................................ 606/59; 606/54
(58) Field of Classification Search .............. 606/53–59, 606/64, 65, 105, 96, 252, 276, 277, 278; 403/364, 385, 90, 110, 374.2; 248/540; 24/490, 24/494; 600/234, 230
See application file for complete search history.

(56) References Cited

U.S. PATENT DOCUMENTS

| | | | | |
|---|---|---|---|---|
| 5,160,335 A | * | 11/1992 | Wagenknecht | 606/59 |
| 5,951,556 A | | 9/1999 | Faccioli et al. | |
| 6,729,794 B2 | * | 5/2004 | Callaway et al. | 403/364 |
| 7,608,074 B2 | * | 10/2009 | Austin et al. | 606/54 |
| 7,708,736 B2 | * | 5/2010 | Mullaney | 606/54 |

* cited by examiner

*Primary Examiner* — Pedro Philogene
(74) *Attorney, Agent, or Firm* — Barbara E. Johnson, Esq.

(57) ABSTRACT

A clamp for an external fixation system includes a body having a bottom portion and semi-spherical top portion. The top portion has a threaded bore provided along a longitudinal axis: The clamp includes a clamp assembly having a base with a semi-spherical cavity and a lid positioned over the base to house at least one pin between the base and the lid. The base and the lid have a bore provided along a longitudinal axis thereof. A fastening member is provided that extends through the bore in the base and the lid of the clamp assembly and is secured within the threaded bore of the top portion of the body. The bores in the base and the lid have a diameter that is greater than the diameter of the fastening member.

12 Claims, 11 Drawing Sheets

MULTI-ANGLE CLAMP

CROSS-REFERENCE TO RELATED APPLICATION

This patent application claims priority to, and incorporates herein by reference, U.S. Provisional Application No. 60/937,391 filed Jun. 27, 2007.

BACKGROUND OF THE INVENTION

1. Field of the Invention

The present invention relates, in general, to a multi-angle clamp, and more particularly, to a multi-angle clamp for use in an external fixation system for holding, distracting and compressing bone fragments adjacent to each other.

2. Description of Related Art

In various orthopedic surgical procedures, it is often necessary to secure two or more portions of bone in a relatively fixed relationship to each other. This need is often a result of a fracture which has occurred to the bone. To ensure that the bone can properly regenerate and fuse the fractures of the bone, it is important that the various bone fragments be positioned at the desired location during bone regeneration.

External fixation systems have been developed to compress two bone fragments for effective healing. Such systems can also be used to distract an osteotomy to achieve bone lengthening. In distracting bone fragments, the separation of the bone fragments must take place along a line parallel to the axis of the bone. Additionally, during such a distracting procedure, the surgeon reorients the pins of the external fixation system over time to achieve the desired bone lengthening.

An example of a typical external fixation system is a rail fixation system. Such a rail fixation system includes two clamps positioned on a rail member. In most instances, one of the clamps is stationary and one of the clamps is adjustable. The clamps are used to secure pins that are coupled to bone fragments.

A common problem encountered by the surgeon is orientation of the pins of the two clamps. If the clamp cannot rotate or pivot, all of the pins must be inserted in the same plane and must be parallel to each other. This condition restricts the surgeon in the selection of the best insertion region on the bone for the pins. In addition, it is very difficult and requires a high amount of skill for a surgeon to orient two or more pins exactly parallel to each other in a single plane. In order to alleviate this problem, rail fixation suppliers developed clamps that allow for rotation of the pin holder. This allowed the pins to be oriented in a non-parallel manner; however, the pins still needed to be in the same plane. Accordingly, rail fixation suppliers developed articulating rails. Such rails are adjustable through a joint that allows for one-dimensional pivoting or ball and socket articulation. This added feature allows the surgeon to position the pins in the clamps with less restriction.

An example of such an external fixation system is described in U.S. Pat. No. 5,951,556 to Faccioli et al. This reference discloses a compact external fixation device for the treatment of bone fractures. The fixation device comprises a pair of clamps connected to a central body by respective spherical joints. The spherical joints include a ball that is configured to cooperate with a cavity in each of the clamps. The clamps are designed to clamp bone screws or pins that have previously been surgically inserted in stumps of a fracture.

However, such structures suffer from a variety of limitations. For example, external fixation systems as described above are less rigid, heavier and more costly than external fixation systems that are constructed from a single rail.

Another type of external fixation system is a ring fixation system. In such a system the pins are used primarily to transfer the patient's weight from the foot or ankle to the tibia. The individual pins are seldom inserted in the same plane or parallel to each other. Additionally, in some instances, the rings are tilted in order to control the angle between two bone segments or across a bone joint in order to correct for acquired or congenital bone deformity. The point of insertion of the pins into the patient is critical. Currently, the pins are secured to the ring fixation system by a pin bolt. However, the surgeon needs greater flexibility in orienting each pin beyond the rotation in one-plane that a pin bolt can provide.

SUMMARY OF THE INVENTION

Accordingly, an object of the present invention is to provide a multi-angle clamp that can secure pins that are implanted in different planes and in a non-parallel manner while providing the ability to be secured to a rigid fixture.

The present invention is directed to a clamp for an external fixation system. The clamp includes a body having a bottom portion and semi-spherical top portion. The top portion has a threaded bore provided along a longitudinal axis thereof. The clamp also includes a clamp assembly having a base with a semi-spherical cavity formed in a bottom portion thereof and a lid positioned over the base to house at least one pin between the base and the lid. The cavity is configured to cooperate with the top portion of the body. The base and the lid have a bore provided along a longitudinal axis thereof. A fastening member is provided that extends through the bores in the base and the lid of the clamp assembly and is secured within the threaded bore of the top portion of the body. The bores in the base and the lid have a diameter that is greater than a diameter of the fastening member.

The clamp may further include a washer positioned over the lid having a bore provided along a longitudinal axis thereof. The bore in the base and the lid may have a diameter that is greater than the diameter of the bore in the washer.

The bottom portion of the body may have a threaded bore formed therethrough that is approximately perpendicular to the threaded bore in the top portion. The bottom portion of the body may be coupled to the external fixation system in a moveable fashion via the threaded bore in the bottom portion. Alternatively, the threaded bore in the top portion of the body may extend through the bottom portion of the body. The bottom portion of the body may be coupled to the external fixation system in a stationary fashion via the threaded bore extending through the bottom portion of the body.

The base and the lid may form at least one hole extending perpendicular to the bore in the base and lid when the lid is positioned over the base. The base and the lid may form two parallel holes extending perpendicular to the bore in the base and lid when the lid is positioned over the base.

The present invention is also directed to an external fixation system including a rail member with a first slot and a second slot having a threaded shaft positioned therein; a first, stationary multi-angle clamp positioned within the first slot, a second multi-angle clamp positioned movably within the second slot, and at least one pin secured by one of the first or second multi-angle clamps.

The first multi-angle clamp may include a body having a bottom portion and semi-spherical top portion. The top portion and the bottom portion have a threaded bore provided along a longitudinal axis thereof. The first multi-angle clamp also includes a clamp assembly having a base with a semi-spherical cavity formed in a bottom portion thereof and a lid positioned over the base to house at least one pin between the base and the lid. The cavity is configured to cooperate with the top portion of the body. The base and the lid have a bore provided along a longitudinal axis thereof. A fastening member is provided that extends through the bore in the washer, the bore in the base and the lid of the clamp assembly and secured within the threaded bore of the top portion of the body. The threaded bore of the bottom portion of the body may be configured to receive a bolt to secure the first multi-angle clamp within the first slot in a stationary manner. The first multi-angle clamp may further include a washer positioned over the lid having a bore provided along a longitudinal axis thereof.

The second multi-angle clamp may include a body having a bottom portion and semi-spherical top portion. The top portion has a threaded bore provided along a longitudinal axis thereof, and the bottom portion has a threaded bore formed therethrough that is approximately perpendicular to the threaded bore in the top portion. The second multi-angle clamp also includes a clamp assembly having a base with a semi-spherical cavity formed in a bottom portion thereof and a lid positioned over the base to house at least one pin between the base and the lid. The cavity is configured to cooperate with the top portion of the body. The base and the lid have a bore provided along a longitudinal axis thereof. A fastening member is provided that extends through the bore in the washer, the bore in the base and the lid of the clamp assembly, and secured within the threaded bore of the top portion of the body. The threaded bore formed in the bottom portion of the body may be configured to engage the threaded shaft positioned in the second slot, thereby allowing the second multi-angle clamp to move along the threaded shaft within the second slot. The second multi-angle clamp may further include a washer positioned over the lid having a bore provided along a longitudinal axis thereof.

The rail member may include a ball and joint hinge between the first and second slots. However, this is not to be construed as limiting the present invention, as it has been envisioned that the ball and joint hinge may be provided on either side of the rail member and may also be cascaded.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. As used in the specification and the claims, the singular form of "a", "an", and "the" include plural referents unless the context clearly dictates otherwise.

DETAILED DESCRIPTION OF THE PRESENT INVENTION

Figure 1:
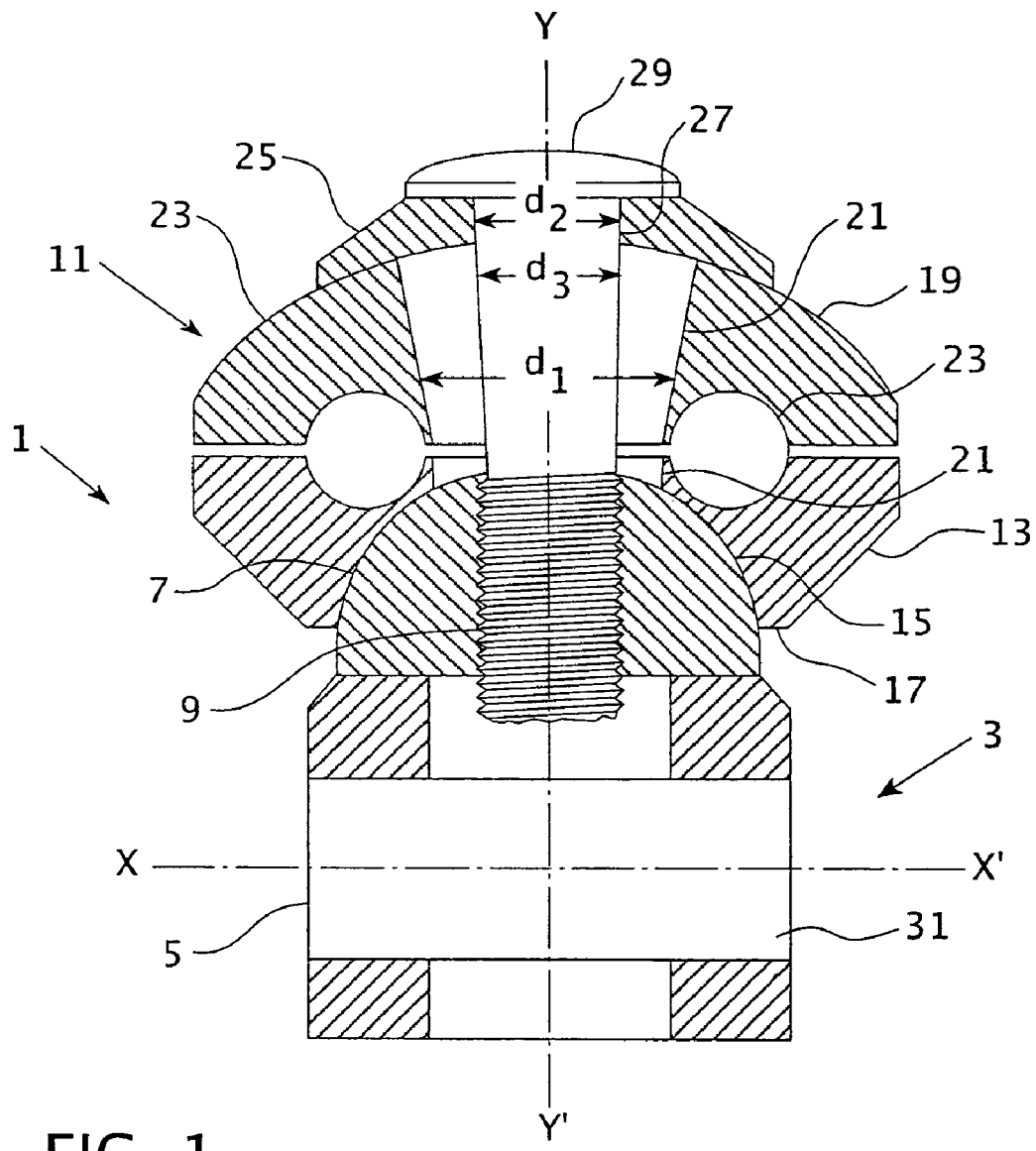
FIG. 1 is a cross-sectional front-view of a multi-angle clamp in accordance with the present invention.

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Figure 2:
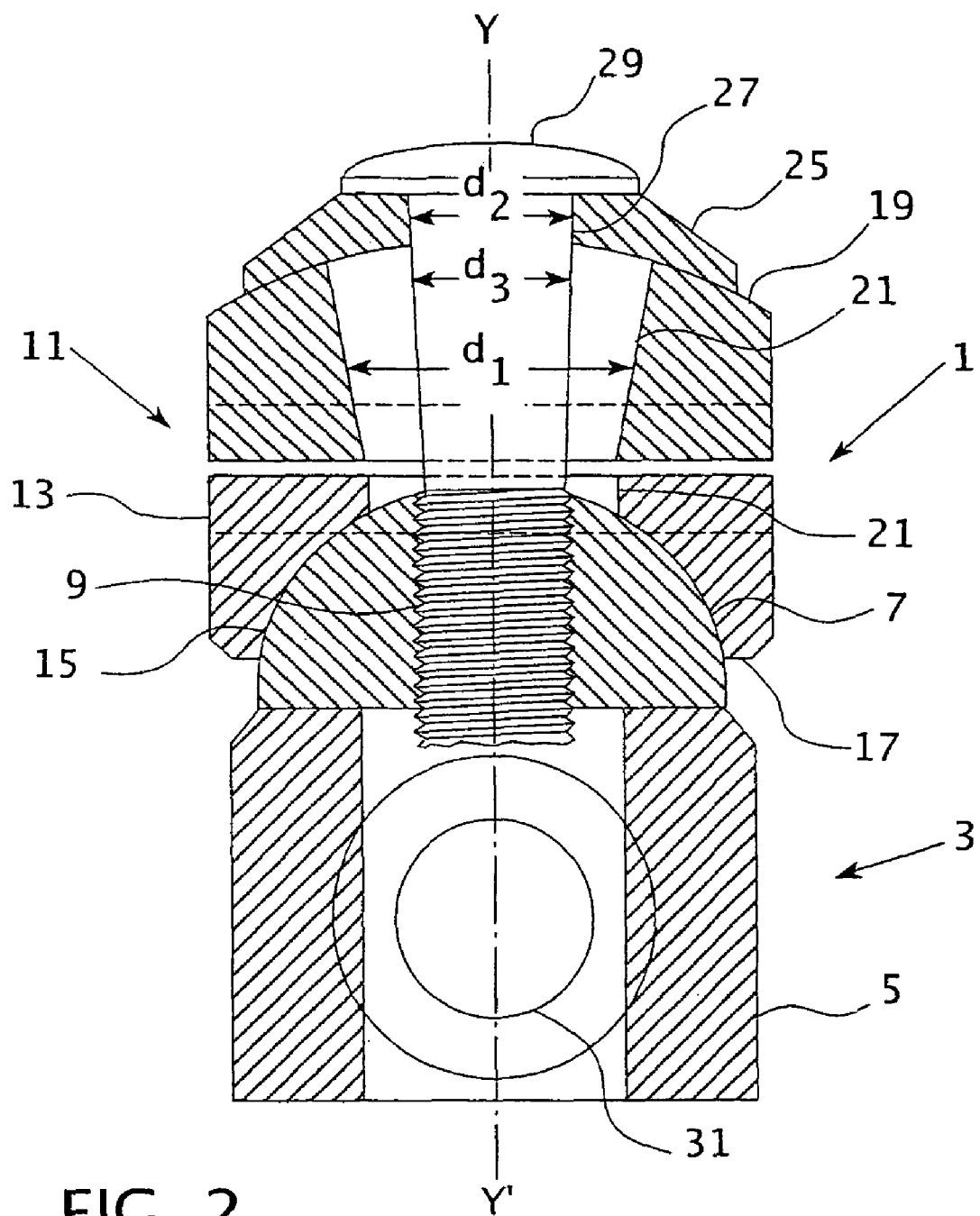
FIG. 2 is a cross-sectional side-view of the multi-angle clamp of FIG. 1.

With reference to FIGS. 1 and 2, a multi-angle clamp, denoted generally as reference numeral 1, includes a body, denoted generally as reference numeral 3, having a bottom portion 5 and a top portion 7. Top portion 7 is shaped like a half sphere or semi-spherical. Body 3 is constructed from stainless steel, aluminum, titanium or any other metal or plastic that is capable of being shaped by machining, casting or forging and has sufficient strength to withstand the force transmitted by the pins. Additionally, bottom portion 5 and top portion 7 may be constructed as a single unitary component to form body 3, or each portion may be formed separately and bonded together. Top portion 7 has a threaded bore 9 provided along a longitudinal axis Y-Y' thereof.

Clamp 1 also includes a clamp assembly, denoted generally as reference numeral 11. Clamp assembly 11 has a base 13 with a semi-spherical cavity 15 formed in a bottom portion 17 thereof and a lid 19 positioned over base 13. Semi-spherical cavity 15 is configured to cooperate with semi-spherical top portion 7 of body 3. Base 13 and lid 19 have a bore 21 provided along a longitudinal axis Y-Y' thereof. Lid 19 and base 13 are configured to form at least one hole, and desirable two holes 23, extending perpendicular to bore 21 in base 13 and lid 19 when lid 19 is positioned over base 13. Holes 23 are desirably positioned parallel to each other and are configured to fixedly house at least one pin between base 13 and lid 19. Accordingly, a single fastening member 29 can simultaneously secure clamp assembly 11 to top portion 7 of body 3 and a least one pin in hole 23.

Clamp assembly 11 is constructed from stainless steel, aluminum, titanium or any other metal or plastic that is capable of being shaped by machining, casting or forging and has sufficient strength to withstand the force transmitted by the pins. Additionally, body 3 and clamp assembly 11 may be constructed from the same or different materials. Clamp 1 further includes a washer 25 positioned over lid 19 having a bore 27 provided along a longitudinal axis Y-Y' thereof. Bore 21 in base 13 and lid 19 has a diameter $d_1$ that is greater than diameter $d_2$ of bore 27 in washer 25. Clamp 1 also includes a fastening member 29. Fastening member 29 extends through bore 27 in washer 25, bore 21 in base 13 and lid 19 of clamp assembly 11 and is secured within threaded bore 9 of top portion 7 of body 3. The fastening member may be a bolt, a screw or any other suitable fastening mechanism. Diameter $d_1$ of bore 21 in base 13 and lid 19 is considerably larger than a diameter $d_3$ of fastening member 29. This allows clamp assembly 11 to be positioned off-center with respect to fastening member 29 and top portion 7 of body 3, and yet rigidly secured to the top portion 7 of body 3. Fastening member 29 also fixedly secures the pins positioned in holes 23 between base 13 and lid 19.

Bottom portion 5 of body 3 further includes a threaded bore 31 formed therethrough, extending along axis X-X' that is approximately perpendicular to threaded bore 9 in top portion 7 of body 3. Bottom portion 5 of body 3 is thereby coupled to an external fixation system in a moveable fashion via threaded bore 31 in bottom portion 5, as will be discussed in greater detail hereinafter.

Figure 3:
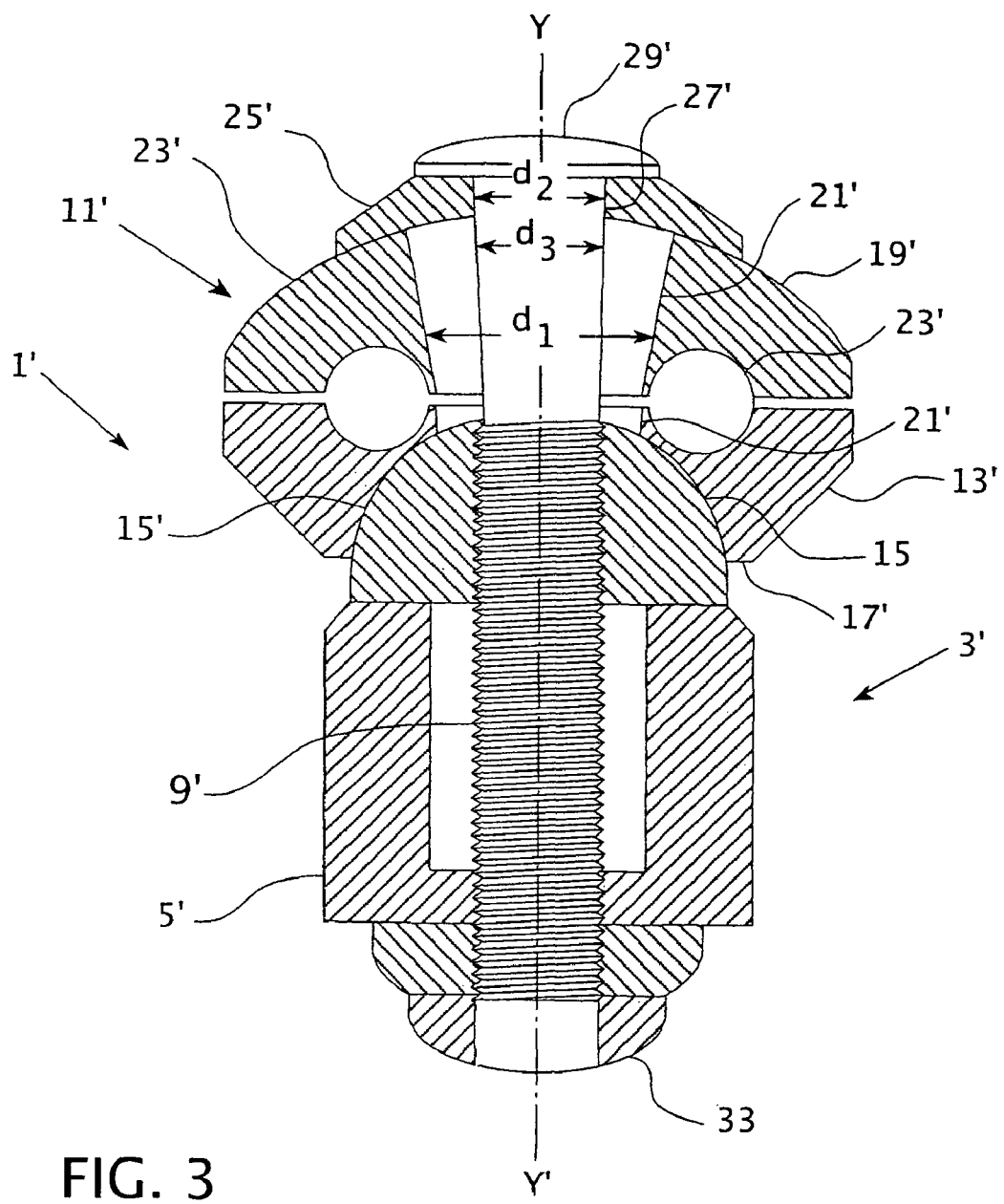
FIG. 3 is a cross-sectional front-view of an alternative embodiment of a multi-angle clamp in accordance with the present invention.

With reference to FIG. 3, and continuing reference to FIGS. 1 and 2, an alternative embodiment of clamp 1' includes a body, denoted generally as reference numeral 3', having a bottom portion 5' and a top portion 7'. Top portion 7' is shaped like a half sphere or semi-spherical. Top portion 7' has a threaded bore 9' provided along a longitudinal axis Y-Y' thereof. Threaded bore 9' in top portion 7' of body 3' extend through bottom portion 5' of body 3'. Bottom portion 5' of body 3' is coupled to an external fixation system in a stationary fashion via threaded bore 9' extending through bottom portion 5' of body 3' by a fastening member 33, as will be discussed in greater detail hereinafter.

Clamp 1' also includes a clamp assembly, denoted generally as reference numeral 11'. Clamp assembly 11' has a base 13' with a semi-spherical cavity 15' formed in a bottom portion 17' thereof, and a lid 19' positioned over base 13'. Semi-spherical cavity 15' is configured to cooperate with semi-spherical top portion 7' of body 3'. Base 13' and lid 19' have a bore 21' provided along a longitudinal axis Y-Y' thereof. Lid 19' and base 13' are configured to form at least one hole, and desirably two holes 23', extending perpendicular to bore 21' in base 13' and lid 19' when lid 19' is positioned over base 13'. Holes 23' are desirably positioned parallel to each other and are configured to fixedly house at least one pin between base 13' and lid 19'.

Clamp 1' further includes a washer 25' positioned over lid 19' having a bore 27' provided along a longitudinal axis Y-Y' thereof. Bore 21' in base 13' and lid 19' has a diameter $d_1$ that is greater than diameter $d_2$ of bore 27' in washer 25'. Clamp 1' also includes a fastening member 29'. Fastening member 29' extends through bore 27' in washer 25', bore 21' in base 13' and lid 19' of clamp assembly 11' and is secured within threaded bore 9' of top portion 7' of body 3'. Diameter $d_1$ of bore 21' in base 13' and lid 19' is considerably larger than diameter $d_3$ of fastening member 29'. This allows clamp assembly 11' to be positioned off-center with respect to fastening member 29' and top portion 7' of body 3', and yet rigidly secured to the top portion 7' of body 3'. Fastening member 29' also fixedly secures the pins positioned in holes 23' between base 13' and lid 19'.

Figure 4:
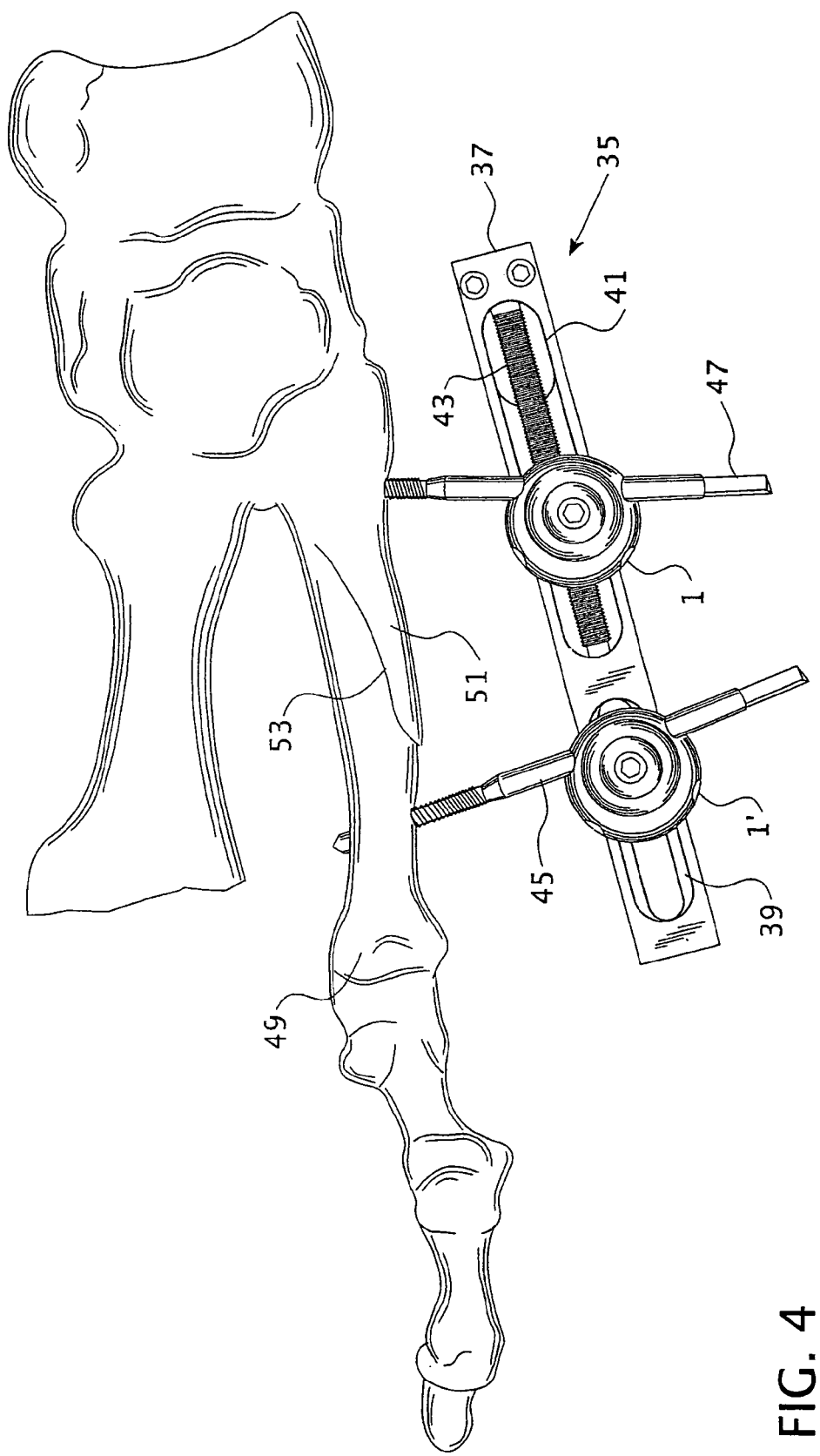
FIG. 4 is a top plan view of an external rail fixation system in accordance with the present invention.
Figure 5:
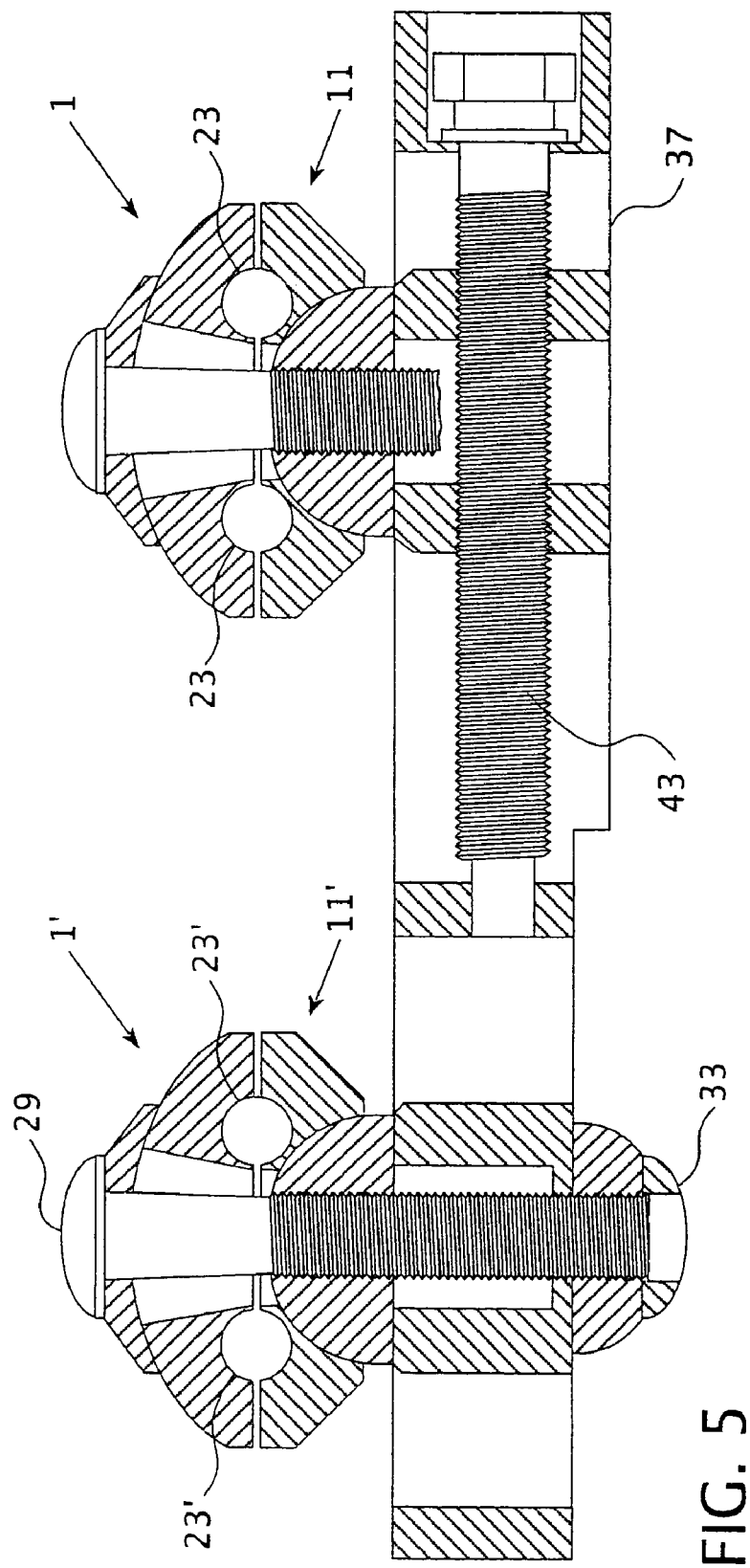
FIG. 5 is a cross-sectional side-view of the external fixation system of FIG. 4.
Figure 6:
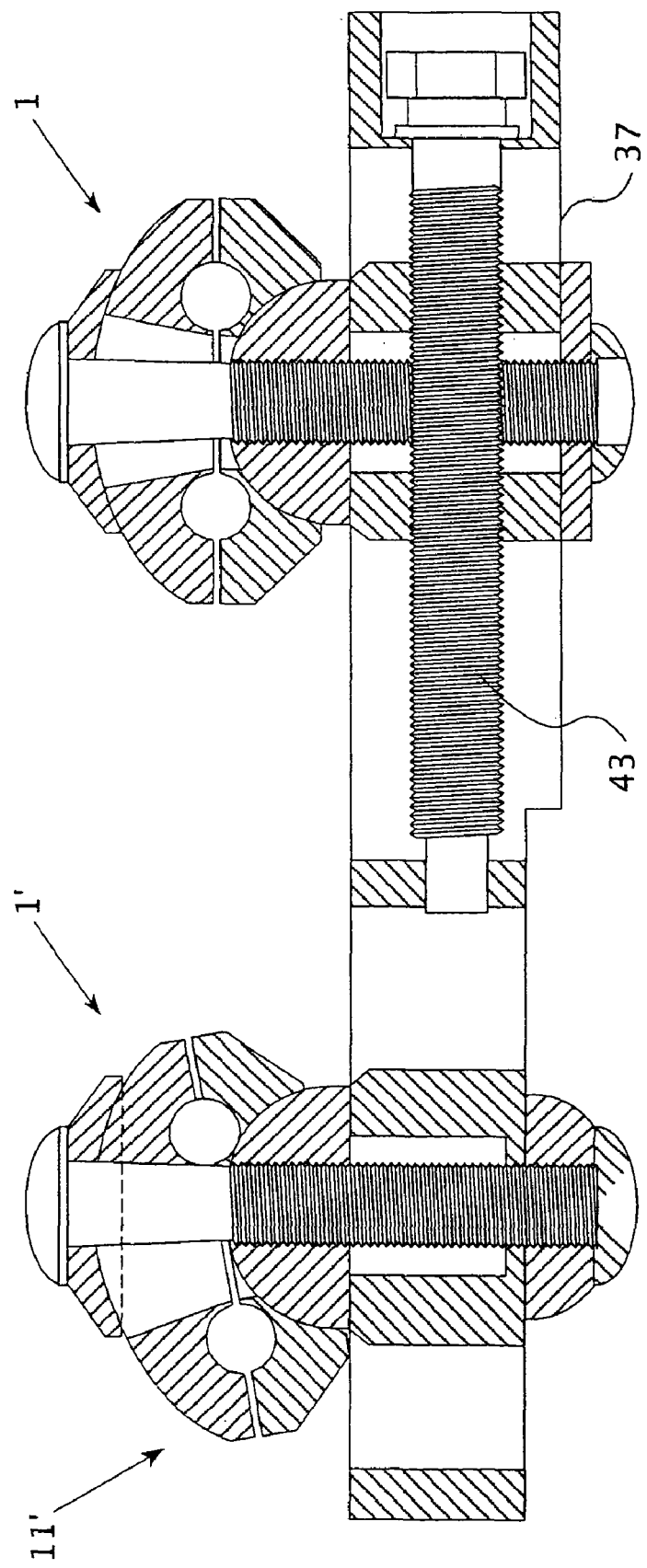
FIG. 6 is a cross-sectional side-view of the external fixation system of FIG. 4 with one of the multi-angle clamps in a tilted configuration.

With reference to FIGS. 4-6, and with continuing reference to FIGS. 1-3, an external rail fixation system, denoted generally as reference numeral 35, includes a rail member 37 with a first slot 39 and a second slot 41 having a threaded shaft 43 positioned therein. A first, stationary multi-angle clamp 1' is positioned within first slot 39 and a second multi-angle clamp 1 is positioned movably within second slot 41. Rail fixation system 35 also includes a first pin 45 secured by first multi-angle clamps 1', and a second pin 47 secured by second multi-angle clamp 1. The pins may be threaded or smooth and are desirably Vilex 500 series half pins manufactured by Vilex, 345 Old Curry Hollow Rd., Pittsburgh, Pa. 15236.

In operation, a surgeon implants first pin 45 into a first bone fragment 49 and a second pin 47 into a second bone fragment 51 of a fracture 53. Next, first multi-angle clamp 1' is fixedly secured within first slot 39 of rail member 37 by placing clamp 1' within slot 39, and securing it therein with fastening member 33. Thereafter, second multi-angle clamp 1 is coupled within second slot 41 to threaded shaft 43 by positioning threaded shaft 43 within threaded bore 31 of clamp 1. Clamp 1 is thereby able to move through second slot 41 by rotating threaded shaft 43.

First pin 45 is then positioned within one of holes 23' of clamp assembly 11' of first clamp 1' and secured therein by tightening fastening member 29' while second pin 47 is positioned within one of holes 23 of clamp assembly 11 of second clamp 1 and secured therein by tightening fastening member 29'. Next, as illustrated in FIG. 6, clamp assembly 11 or 11' may be rotated or pivoted. By rotating or pivoting clamp assembly 11 or 11' with respect to body 3 or 3', the pins 45 and 47 may be oriented in any direction within the allowable range of motion of the device. This provides the surgeon with greater options for inserting the pins into the bone fragments of a patient leading to more efficient surgeries. Finally, the clamp assemblies 11 and 11' are secured to the bodies 3 and 3' by completely tightening fastening members 29 and 29'.

Figure 7:
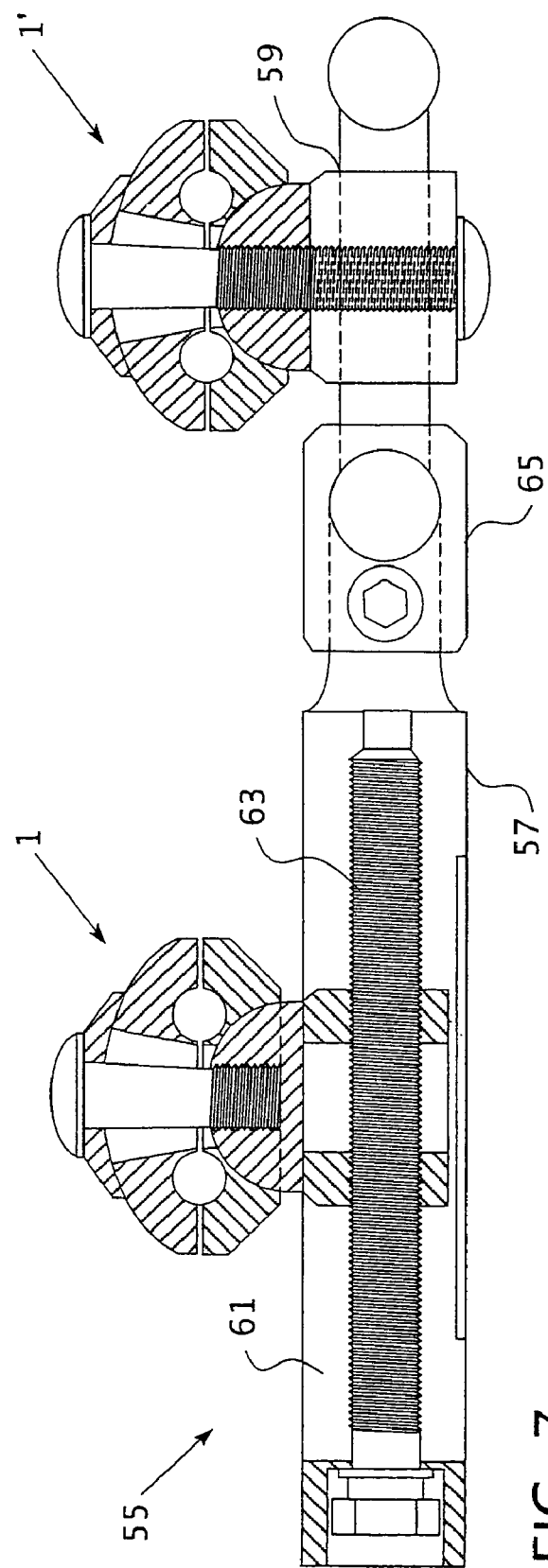
FIG. 7 is a cross-sectional side-view of an alternative embodiment of an external fixation system in accordance with the present invention.

With reference to FIG. 7, and with continuing reference to FIGS. 1-3, an alternative embodiment of an external rail fixation system, denoted generally as reference numeral 55 is illustrated. External rail fixation system 55 includes a rail member 57 with a first slot 59 and a second slot 61 having a threaded shaft 63 positioned therein. First slot 59 and second slot 61 of rail member 57 are separated by a ball-and-joint hinge 77. This additional hinge provides the surgeon with even more flexibility in positioning the pins within the patient. A first, stationary multi-angle clamp 1' is positioned within first slot 59 and a second multi-angle clamp 1 is positioned movably within second slot 61.

Figure 8:
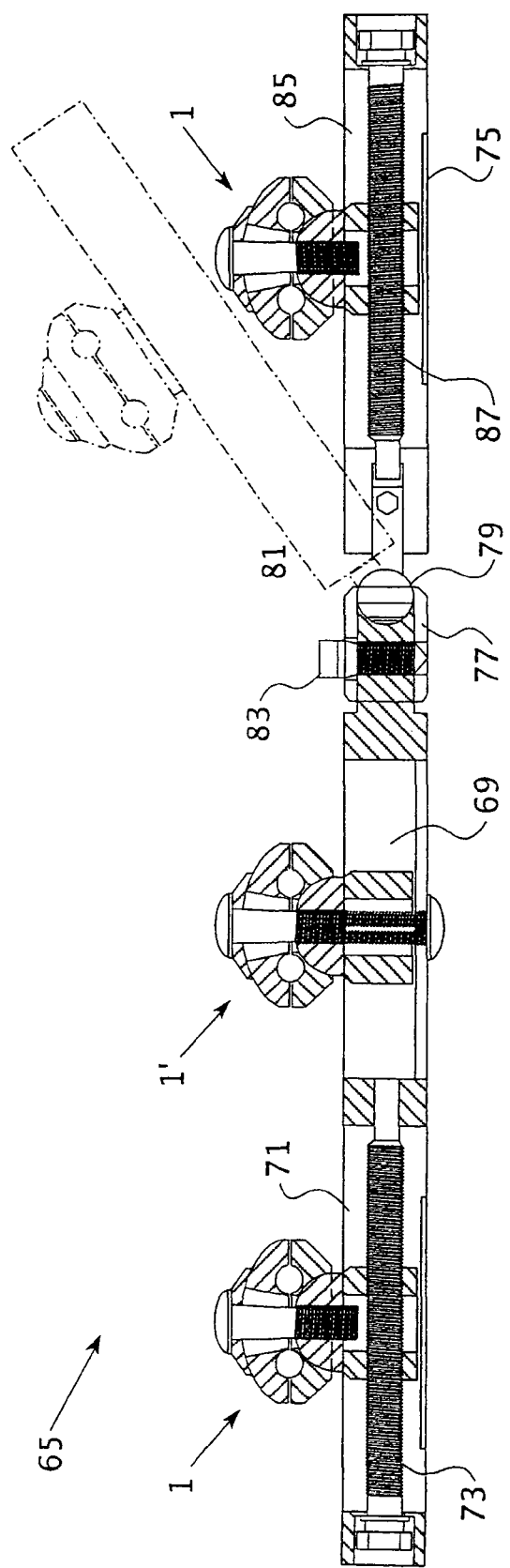
FIG. 8 is a cross-sectional side-view of another alternative embodiment of an external fixation system in accordance with the present invention.

With reference to FIG. 8, and with continuing reference to FIGS. 1-4, another alternative embodiment of an external rail fixation system, denoted generally as reference numeral 65, includes a first rail member 67 with a first slot 69 and a second slot 71 having a threaded shaft 73 positioned therein. A first, stationary multi-angle clamp 1' is positioned within first slot 69 and a second multi-angle clamp 1 is positioned movably within second slot 71.

Rail fixation system 65 further includes a second rail member 75 coupled to first rail member 67 via a ball-and-joint hinge 77. Ball-and-joint hinge 77 includes a ball member 79 coupled to second rail member 75, and a socket member 81 coupled to first rail member 67 by a fastening member 83. Fastening member 83 may be a screw, bolt or any other suitable fastening mechanism. Ball-and-joint hinge 77 provides the surgeon with even more flexibility in positioning the pins within the patient. Second rail member 75 includes a slot 85 having a threaded shaft 87 therein. A third, movable multi-angle clamp 1 is positioned within slot 85.

Figure 9:
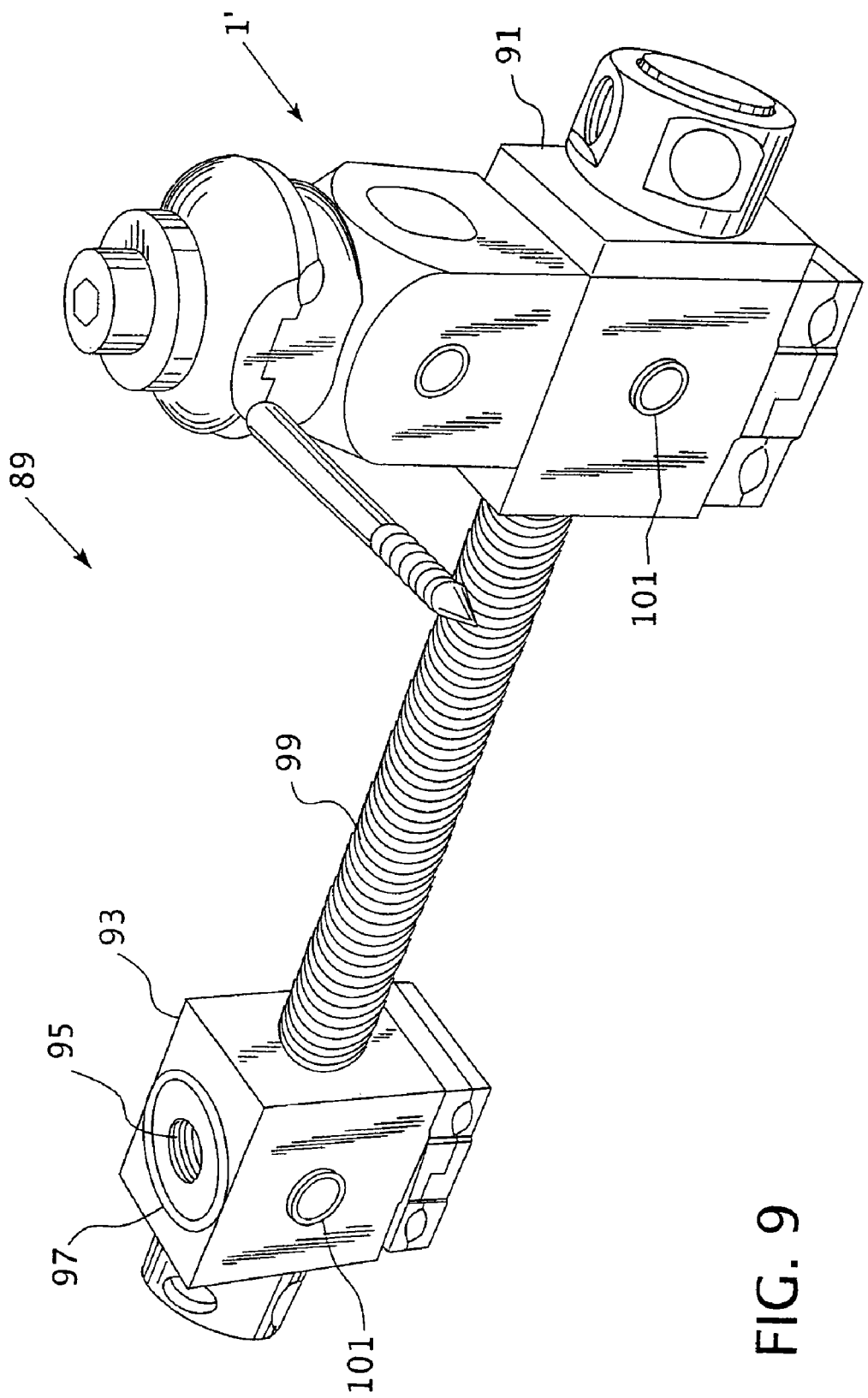
FIG. 9 is a perspective view of an additional alternative embodiment of an external fixation system in accordance with the present invention.

With reference to FIG. 9, and with continuing reference to FIG. 3, an additional alternative embodiment of an external rail fixation system, denoted generally as reference numeral 89, includes a first carriage 91 and a second carriage 93 that is identical to the first carriage. Each of the carriages 91, 93 are include a threaded bore 95 on a top surface 97 thereof to secure a multi-angle clamp 1' thereon. Carriages 91, 93 are designed to move along a threaded shaft 99 and are secured to the threaded shaft by set screws 101.

External rail fixation system 89 is larger than the previously described embodiments and is designed for use in securing larger, more severe fractures.

Figure 10:
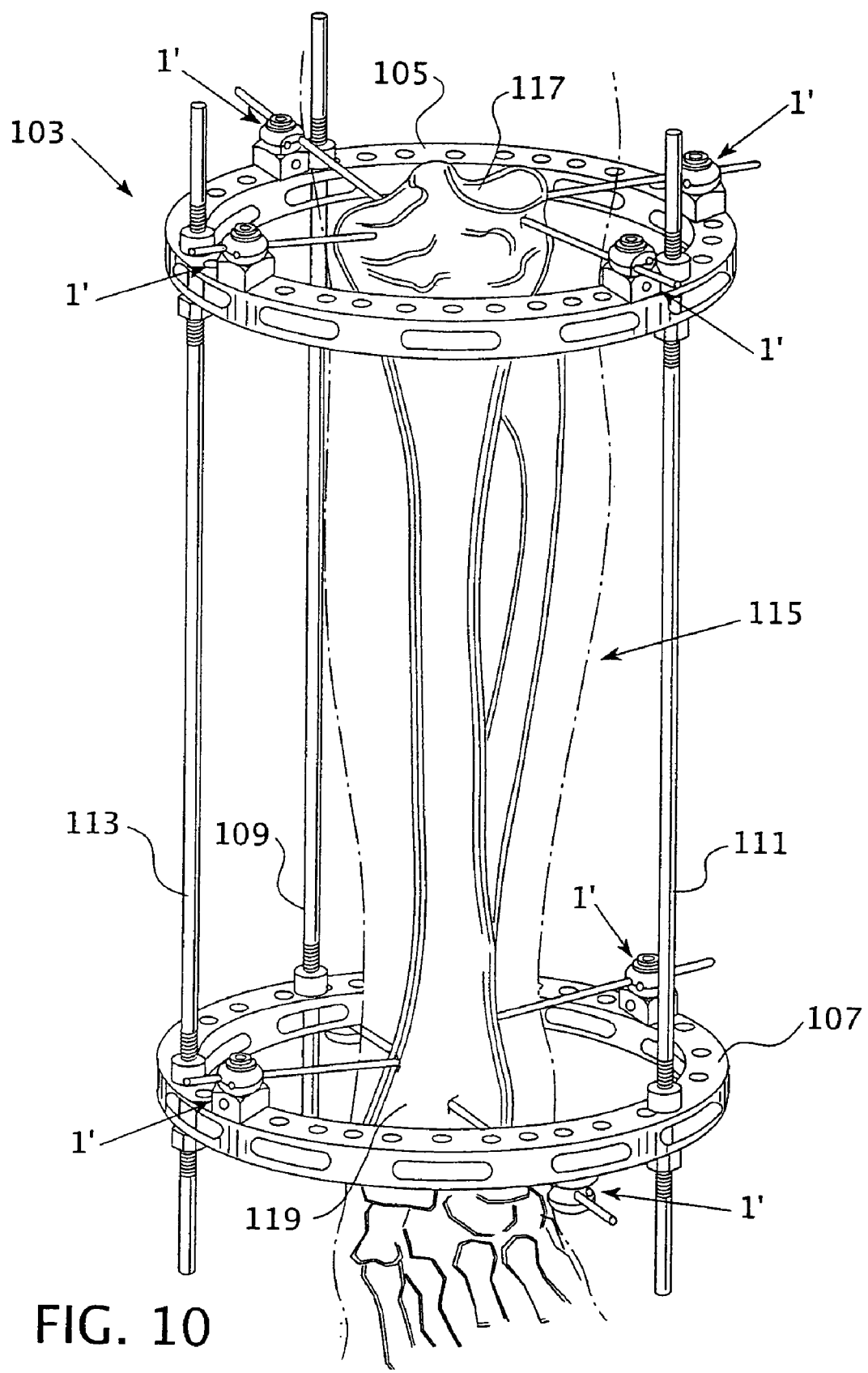
FIG. 10 is a perspective view of a rail fixation system utilizing a multi-angle clamp in accordance with the present invention.
Figure 11:
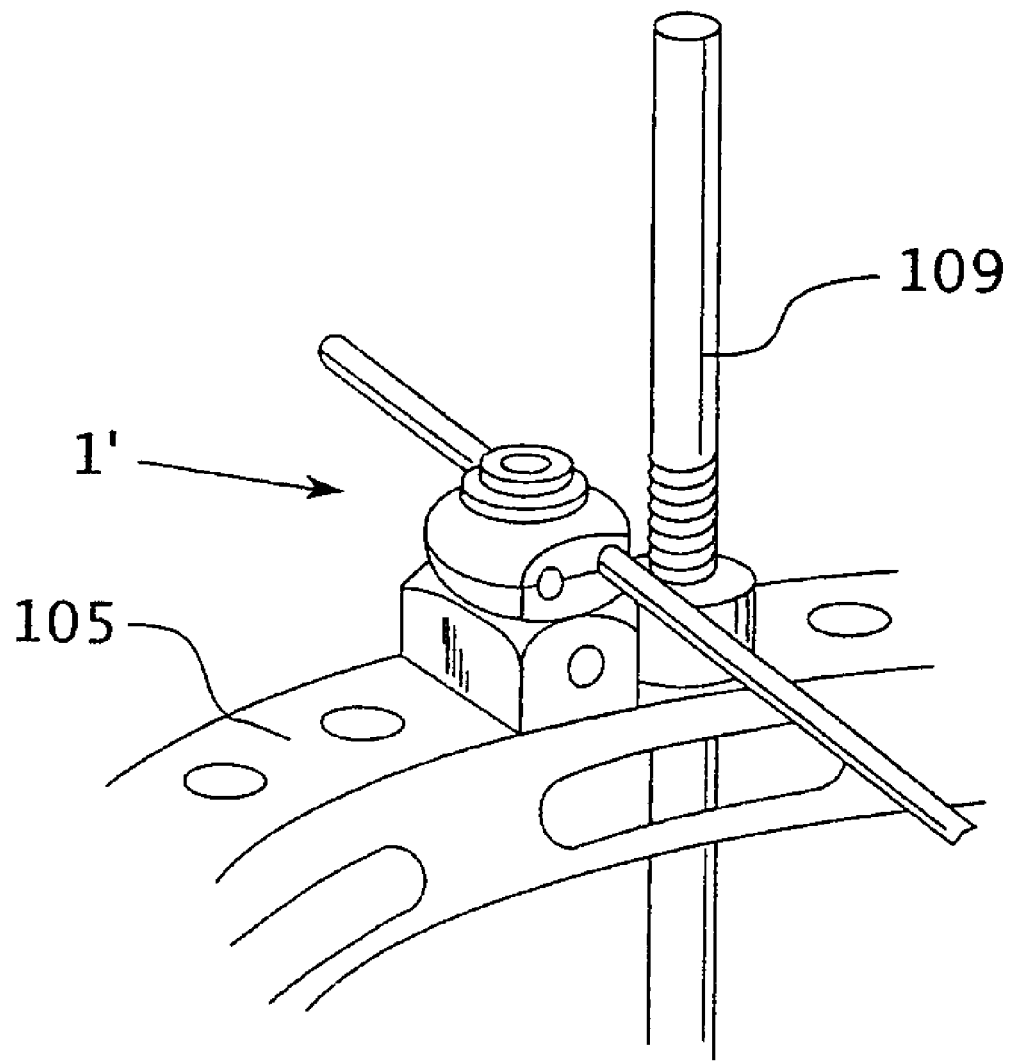
FIG. 11 is a portion of a view of the rail fixation system of FIG. 10 enlarged for magnification purposes.

With reference to FIGS. 10 and 11, and with continuing reference to FIG. 3, multi-angle clamp 1' of the present invention may also be utilized as a part of an external ring fixation system, denoted generally as reference numeral 103. External ring fixation system 103 includes a pair of rings, namely a proximal ring 105 and a distal ring 107, and three tie rods 109, 111 and 113 connecting rings 105 and 107 together. A series of multi-angle clamps 1' are positioned around each of rings 105 and 107.

In use, rings 105 and 107 are positioned around the lower leg 115 of a patient. Each end 117, 119 of the lower leg 115 of the patient is secured to each ring 105 and 107, respectively, by means of appropriate linking elements 121. Linking elements 121 may be in the form of wires, as shown in the figures, screws, pins or any other suitable linking mechanism. Such a system 103 may be used to set a fracture or to transfer the patient's weight from the foot or ankle to the tibia.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. Furthermore, it is to be understood that the present invention contemplates that, to the extent possible, one or more features of any embodiment can be combined with one or more features of any other embodiment.

The invention claimed is:

1. A clamp for an external fixation system comprising: a body having a bottom portion and semi-spherical top portion, the top portion having a threaded bore provided along a longitudinal axis thereof; a clamp assembly comprising: a base with a semi-spherical cavity formed in a bottom portion thereof, the cavity configured to cooperate with the top portion of the body; and a lid positioned over the base to house at least one pin between the base and the lid, the base and the lid having a bore provided along a longitudinal axis thereof; and a fastening member extending through the bore in the base and the lid of the clamp assembly and secured within the threaded bore of the top portion of the body, wherein the bore in the base and the lid has a diameter that is greater than a diameter of the fastening member.

2. The clamp of claim 1, wherein the bottom portion of the body has a threaded bore formed therethrough that is approximately perpendicular to the threaded bore in the top portion.

3. The clamp of claim 2, wherein the bottom portion of the body is coupled to the external fixation system via the threaded bore in the bottom portion.

4. The clamp of claim 3, wherein the bottom portion of the body is coupled to the external fixation system in a moveable fashion.

5. The clamp of claim 1, wherein the threaded bore in the top portion of the body extends through the bottom portion of the body.

6. The clamp of claim 5, wherein the bottom portion of the body is coupled to the external fixation system via the threaded bore extending through the bottom portion of the body.

7. The clamp of claim 6, wherein the bottom portion of the body is coupled to the external fixation system in a stationary fashion.

8. The clamp of claim 1, wherein the base and the lid form at least one hole extending perpendicular to the bore in the base and lid when the lid is positioned over the base.

9. The clamp of claim 8, wherein the base and the lid form two holes extending perpendicular to the bore in the base and lid when the lid is positioned over the base.

10. The clamp of claim 9, wherein the two holes are parallel to each other.

11. The clamp of claim 1, further comprising: a washer positioned over the lid having a bore provided along a longitudinal axis thereof.

12. The clamp of claim 11, wherein the bore in the base and the lid has a diameter that is greater than the diameter of the bore in the washer.

* * * * *